(12) United States Patent
Schlegel et al.

(10) Patent No.: US 11,696,594 B2
(45) Date of Patent: *Jul. 11, 2023

(54) VITAMIN FORMULATION

(71) Applicant: DSM IP ASSETS B.V., Heerlen (NL)

(72) Inventors: Bernd Schlegel, Kaiseraugst (CH);
Loni Schweikert, Kaiseraugst (CH);
Olivia Vidoni, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 64 days.

This patent is subject to a terminal disclaimer.

(21) Appl. No.: 15/775,425

(22) PCT Filed: Dec. 9, 2016

(86) PCT No.: PCT/EP2016/080421
§ 371 (c)(1),
(2) Date: May 11, 2018

(87) PCT Pub. No.: WO2017/097974
PCT Pub. Date: Jun. 15, 2017

(65) Prior Publication Data
US 2018/0343909 A1    Dec. 6, 2018

(30) Foreign Application Priority Data
Dec. 10, 2015 (EP) .................................... 15199204

(51) Int. Cl.
*A61K 8/67*   (2006.01)
*A61K 47/36*  (2006.01)
(Continued)

(52) U.S. Cl.
CPC ............. *A23L 33/155* (2016.08); *A23L 29/10* (2016.08); *A23L 29/219* (2016.08); *A23L 29/25* (2016.08);
(Continued)

(58) Field of Classification Search
CPC ...... A23L 33/155; A23L 29/10; A23L 33/125; A23L 29/219; A23L 29/25; A23L 33/15;
(Continued)

(56) References Cited

U.S. PATENT DOCUMENTS

2006/0252761 A1* 11/2006 Davis ................... A61K 31/498
514/250
2007/0173547 A1   7/2007 Feldthusen Jensen
(Continued)

FOREIGN PATENT DOCUMENTS

| CN | 1642106 A | 7/2005 |
|---|---|---|
| CN | 101023140 A | 8/2007 |
| JP | 2014-534959 | 12/2014 |

OTHER PUBLICATIONS

International Search Report for PCT/EP2016/080421, dated Oct. 31, 2017, 4 pages.
(Continued)

*Primary Examiner* — W A Moore
(74) *Attorney, Agent, or Firm* — Nixon & Vanderhye P.C.

(57) ABSTRACT

The present patent application relates to solid particles comprising at least one fatsoluble vitamin, which are more stable when compressed into tablets.

4 Claims, 3 Drawing Sheets

1: particles with food modified starches and maltodextrin 12 ;
2: particles with food modified starches and maltodextrin 20-23,
3: particles with food modified starches and trehalose

(51) Int. Cl.

| | |
|---|---|
| *A61K 9/20* | (2006.01) |
| *A23L 33/155* | (2016.01) |
| *A23L 29/10* | (2016.01) |
| *A23P 10/28* | (2016.01) |
| *A23L 29/219* | (2016.01) |
| *A23L 29/25* | (2016.01) |
| *A23L 33/15* | (2016.01) |
| *A23L 33/125* | (2016.01) |

(52) U.S. Cl.
CPC ............ *A23L 33/125* (2016.08); *A23L 33/15* (2016.08); *A23P 10/28* (2016.08); *A61K 8/671* (2013.01); *A61K 9/2018* (2013.01); *A61K 47/36* (2013.01); *A23V 2002/00* (2013.01)

(58) Field of Classification Search
CPC ...... A23V 2250/636; A23V 2250/5118; A23V 2250/2028; A23V 2250/702; A23P 10/28
USPC .......................................................... 426/73
See application file for complete search history.

(56) References Cited

U.S. PATENT DOCUMENTS

| | | | |
|---|---|---|---|
| 2008/0026124 A1 | 1/2008 | Musaeus et al. | |
| 2008/0089941 A1* | 4/2008 | Mower ................ | A61K 45/06 424/489 |
| 2008/0102131 A1* | 5/2008 | Nagira ................ | A61K 31/355 424/489 |
| 2008/0299209 A1* | 12/2008 | Beck ................... | A61K 8/0241 424/490 |
| 2009/0029028 A1* | 1/2009 | Garcin ................ | A61K 33/34 426/648 |
| 2009/0105331 A1* | 4/2009 | Schaffner .............. | A23L 33/155 514/458 |
| 2011/0015219 A1* | 1/2011 | Trawick ................ | A61P 35/00 514/278 |
| 2011/0052707 A1* | 3/2011 | Buck .................... | A61K 9/1617 424/490 |
| 2013/0195983 A1* | 8/2013 | Desai ..................... | A61P 35/00 424/491 |
| 2014/0242179 A1* | 8/2014 | Diguet .................. | A23K 40/30 424/498 |

OTHER PUBLICATIONS

Written Opinion of the ISA for PCT/EP2016/080421, dated Oct. 31, 2017, 8 pages.

Elizalde et al., "Retention of .Beta.-Carotene Encapsulated in a Trehalose-Based Matrix as Affected by Water Content and Sugar Crystallization", Journal of Food Science, vol. 6 7, No. 8, Oct. 1, 2002, pp. 2039-3045.

Lim et al., "Stability and Loss Kinetics of Lutein and B-Carotene Encapsulated in Freeze-Dried Emulsions with Layered Interface and Trehalose as Glass Former", Food Research International, vol. 62, Apr. 2014, pp. 403-409.

Notice of Reasons for Rejection regarding with JP Appln No. P2018-525440 (with English-language translation) dated Jul. 21, 2020.

CN Application No. 201680070628.6, The First Office Action, dated Jan. 6, 2021.

CN Application No. 201680070628.6, The Second Office Action with English-language Translation, dated Jun. 30, 2021.

Li et al, "Factors Influencing the Degradation of Drug Preparations and Stability Measures," Wuhan: Hubei Science & Technology Press, Feb. 2014, English-language Translation.

* cited by examiner

1: particles with food modified starch and maltodextrin 12;

2: particles with food modified starch and trehalose;

3: particles with food modified starch and sucrose

1: particles with food modified starches and maltodextrin 12 ;

2: particles with food modified starches and maltodextrin 20-23,

3: particles with food modified starches and trehalose

1: particles with gum acacia and maltodextrin 20-23 ;

2: particles with gum acacia and maltodextrin 12,

3: particles with gum acacia and trehalose

US 11,696,594 B2

VITAMIN FORMULATION

CROSS-REFERENCE TO RELATED APPLICATIONS

This application is the U.S. national phase of International Application No. PCT/EP2016/080421 filed 9 Dec. 2016, which designated the U.S. and claims priority to EP Patent Application No. 15199204.7 filed 10 Dec. 2015, the entire contents of each of which are hereby incorporated by reference.

FIELD

The present patent application relates to solid particles comprising a high amount of at least one fat-soluble vitamin, which are more stable when compressed into tablets. Furthermore, the particles can be free of any animal derived ingredient and therefore suitable for vegetarians.

BACKGROUND AND SUMMARY

Compressed tablets are a very useful way for administering fat-soluble vitamins. They are easy to be consumed, easy to store and good to handle.

When compressed tablets are produced, harsh conditions are to be applied. It is clear that a certain pressure has to be used to compress any formulation into a tablet. Therefore, there is usually an issue, that the ingredients, which are part of the formulation, which is used to be compressed, are squeezed out and therefore are not part of the tablet anymore. In other words, the tablet contains usually less of the fat-soluble vitamin in the compressed tablet than in the formulation, which was compressed. Usually the content of the fat-soluble vitamins is getting less during the storage of the compressed tablets.

Gelatine, which is often used to formulate fat-soluble vitamins, is usually sourced from an animal source and therefore not suitable for vegetarians.

Due to the importance of compressed tablets, comprising fat-soluble vitamins, there is always a need for improved compressible formulations.

Surprisingly it was found that such an improvement was achieved by adding one or more non-reducing sugar to the solid formulation, which is used to produce compressed tablets.

DETAILED DESCRIPTION

Figure 1:
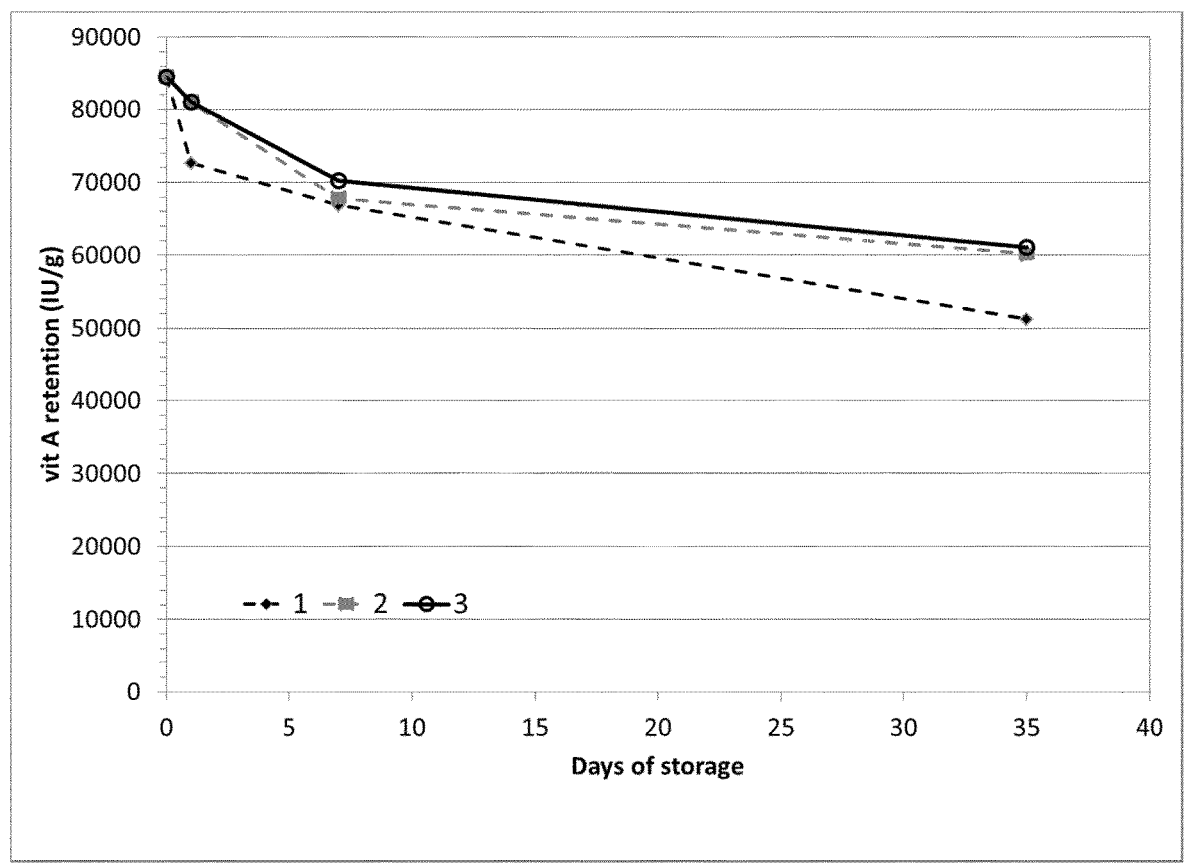
FIGS. 1-3 are each graphs of the data in Tables 5-7, respectively, below showing vitamin A retention (IU/g) versus days of storage.

The embodiments disclosed herein relate to solid particles (SP) comprising:
(i) at least 20 weight-% (wt-%), based on the total weight of the solid particles, of least one fat soluble vitamin,
(ii) at least one emulsifier, and
(iii) at least one non-reducing sugar.

These solid particles show better storage stability (of the fat-soluble vitamin) when compressed into tablets.

It also possible to produce solid particles with only these three kind of ingredients.

Therefore, the present invention relates to solid particles (SP') consisting of
(i) at least 20 weight-% (wt-%), based on the total weight of the solid particles, of least one fat soluble vitamin,
(ii) at least one emulsifier, and
(iii) at least one non-reducing sugar.

Preferred non-reducing sugars are non-reducing disaccharides; more preferably sucrose and/or trehalose, most preferred is trehalose.

Sucrose is a disaccharide combination of the monosaccharides glucose and fructose with the formula $C_{12}H_{22}O_{11}$. It is commercially available from many suppliers.

Sucrose is often extracted and refined from either cane or beet sugar for human

Trehalose, also known as mycose or tremalose, is a natural alpha-linked disaccharide formed by an α,α-1,1-glucoside bond between two α-glucose units. There is an industrial process where trehalose is derived from corn starch. There are known biological pathways for trehalose biosynthesis.

Trehalose is available commercially from various suppliers.

The amount of non-reducing sugar in the solid particles is from 5-55 weight-% (wt-%), based on the total weight of the solid particles. Preferably 10-50 wt-%, based on the total weight of the solid particles; more preferably 15-45 wt-%, based on the total weight of the solid particles.

Therefore the present invention relates to solid particles (SP1), which are solid particles (SP) or (SP') comprising 5-55 wt-%, based on the total weight of the solid particles, of at least one non-reducing sugar.

Therefore the present invention relates to solid particles (SP2), which are solid particles (SP) or (SP') comprising 10-50 wt-%, based on the total weight of the solid particles, of at least one non-reducing sugar.

Therefore the present invention relates to solid particles (SP3), which are solid particles (SP) or (SP') comprising 15-45 wt-%, based on the total weight of the solid particles, of at least one non-reducing sugar.

The solid particles according to the present invention comprise at least one fat-soluble vitamin.

Fat-soluble vitamins are vitamin A, D, E, and K (as well as derivatives thereof). In a preferred embodiment of the present invention, vitamin A and/or its derivatives (such as vitamin A acetate and vitamin A palmitate) are used.

Therefore, the present invention relates to solid particles (SP4), which are solid particles (SP), (SP'), (SP1) or (SP2), wherein the fat-soluble vitamin is vitamin A and/or a derivative of vitamin A (especially vitamin A acetate or vitamin A palmitate).

The solid particles according to the present invention comprise usually comprise 20-75 wt-%, based on the total weight of the solid particles, of at least one fat soluble vitamin, preferably, 25-70 wt-%, based on the total weight of the solid particles.

Therefore, the present invention relates to solid particles (SP5), which are solid particles (SP), (SP'), (SP1), (SP2), (SP3) or (SP4), wherein the solid particles comprise 20-75 wt-%, based on the total weight of the solid particles, of the fat-soluble vitamin(s).

Therefore, the present invention relates to solid particles (SP6), which are solid particles (SP), (SP'), (SP1), (SP2), (SP3), (SP4) or (SP5), wherein the solid particles comprise 25-70 wt-%, based on the total weight of the solid particles, of the fat-soluble vitamin(s).

Furthermore, the solid particles according to the present invention comprise at least one emulsifier. Any commonly known and used emulsifier can be used. A single emulsifier as well as a mixture of emulsifiers can be used.

Suitable emulsifiers are modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), modified gum acacia, TIC gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, and sugar ester (as well as derivatives thereof).

Preferred are emulsifiers, which are not derived from an animal source.

More preferred emulsifiers are modified (food) starches, polysaccharide gums and plant proteins.

The starches can be modified physically and chemically. Pregelatinized starches are examples of physically modified starches. Acidic modified, oxidized, cross-linked, starch esters, starch ethers and cationic starches are examples of chemically modified starches.

The amount of the emulsifier(s) in the solid particles is usually from 20-70 wt-%, based on the total weight of the solid particles; preferably 25-65 wt-%, based on the total weight of the solid particles.

Therefore the present invention relates to solid particles (SP7), which are solid particles (SP), (SP'), (SP1), (SP2), (SP3), (SP4), (SP5) or (SP6), wherein the at least emulsifier is chosen from the group consisting of modified (food) starches, ascorbyl palmitate, pectin, alginate, carrageenan, furcellaran, dextrin derivatives, celluloses and cellulose derivatives (e.g. cellulose acetate, methyl cellulose, hydroxypropyl methyl cellulose), lignosulfonate, polysaccharide gums (such as gum acacia (=gum arabic), modified gum acacia, TIC gum, flaxseed gum, ghatti gum, tamarind gum and arabinogalactan), gelatine (bovine, fish, pork, poultry), plant proteins (such as are for example peas, soybeans, castor beans, cotton, potatoes, sweet potatoes, manioc, rapeseed, sunflowers, sesame, linseed, safflower, lentils, nuts, wheat, rice, maize, barley, rye, oats, lupin and sorghum), animal proteins including milk or whey proteins, lecithin, polyglycerol ester of fatty acids, monoglycerides of fatty acids, diglycerides of fatty acids, sorbitan ester, and sugar ester (as well as derivatives thereof).

Therefore the present invention relates to solid particles (SP7'), which are solid particles (SP), (SP'), (SP1), (SP2), (SP3), (SP4), (SP5) or (SP6), wherein the at least emulsifier is not derived from an animal source.

Therefore the present invention relates to solid particles (SP7"), which are solid particles (SP), (SP'), (SP1), (SP2), (SP3), (SP4), (SP5) or (SP6), wherein the at least emulsifier is chosen from the group consisting of modified (food) starches, polysaccharide gums and plant proteins.

Therefore the present invention relates to solid particles (SP8), which are solid particles (SP), (SP'), (SP1), (SP2), (SP3), (SP4), (SP5), (SP6), (SP7), (SP7') or (SP7"), wherein the amount of the emulsifier(s) in the solid particles is 20-70 wt-%, based on the total weight of the solid particles.

Therefore the present invention relates to solid particles (SP9), which are solid particles SP), (SP'), (SP1), (SP2), (SP3), (SP4), (SP5), (SP6), (SP7), (SP7') or (SP7"), wherein the amount of the emulsifier(s) in the solid particles is 25-65 wt-%, based on the total weight of the solid particles.

Furthermore, the solid particles can comprise further ingredients (auxiliary agents). Such auxiliary agents are for example antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); stabilisers (such as gel-forming agents as xanthan gum, gellan gum); humectants (such as glycerine, sorbitol, polyethylene glycol); dyes; fragrances; fillers and buffers.

These auxiliary agents can be useful for the solid particles, for their production, for the final product (for what the solid particles used) and/or for the production of the final product.

These compounds can optionally be used in an amount of up to 15 wt-%, based on the solid particles.

Therefore the present invention relates to solid particles (SP10), which are solid particles (SP), (SP1), (SP2), (SP3), (SP4), (SP5), (SP6), (SP7), (SP7'), (SP7"), (SP8) or (SP9), comprising up to 15 wt-%, based on the solid particles, of at least one auxiliary agents.

Therefore the present invention relates to solid particles (SP11), which are solid particles (SP10), wherein the auxiliary agent (or auxiliary agents) is chosen from the group consisting of antioxidants (such as ascorbic acid or salts thereof, tocopherol (synthetic or natural)), butylated hydroxytoluene (BHT), ascorbyl palmitate, butylated hydroxyanisole (BHA), propyl gallate, tert. butyl hydroxyquinoline, ethoxyquin and/or ascorbic acid esters of a fatty acid); stabilisers (such as gel-forming agents as xanthan gum, gellan gum); humectants (such as glycerine, sorbitol, polyethylene glycol); dyes; fragrances; fillers and buffers.

Depending on the way of the production of the solid particles according to the present invention it also possible that they are coated with a powder, which is used in the powder catch process. Such a powder can be for example corn starch.

The amount of the powder (especially of corn starch) can be up to 15 wt-%, based on the total weight of the powder coated particles. Usually the content of the powder coating is kept as low as possible, so that another coating layer can be created.

Furthermore, it is also possible to coat the solid particles with a coating layer. This layer can be of any known and used coating material.

A suitable size of the solid particles of the present invention is between 50-1000 μm (preferably 100-800 μm); the size is defined by the diameter of the longest dimension of the particle and measured by commonly known method (like laser diffraction) All particle sizes of the solid particles according to the present invention are determined by laser diffraction technique using a "Mastersizer 3000" of Malvern Instruments Ltd., UK. Further information on this particle size characterization method can e.g. be found in "Basic principles of particle size analytics", Dr. Alan Rawle, Malvern Instruments Limited, Enigma Business Part, Grovewood Road, Malvern, Worcestershire, WR14 1XZ, UK and the "Manual of Malvern particle size analyzer". Particular reference is made to the user manual number MAN 0096, Issue 1.0, November 1994. If nothing else is stated all particle sizes referring to the coarse particles of the solid particles according to the present invention are Dv90 values (volume diameter, 90% of the population resides below this point, and 10% resides above this point) determined by laser diffraction. The particle size can be determined in the dry form, i.e. as powder or in suspension. Preferably, the particle size of the solid particles according to the present invention is determined as powder.

The distribution of the particle size of the solid particles is also no essential feature of the present invention.

The shape of the solid particles is also not an essential feature of the present invention. The shape can be sphere-like or any other form (also mixtures of shapes). Usually and preferably, the particles are sphere-like.

The particles can be produced by any commonly known process, which are used to produce such particles (spray drying, spray chilling, etc.).

The process of coating such small particles is well known. It is usually done by fluidized bed spray granulation, film coating or wet granulation.

The solid particles according to the present invention are mainly used for producing compressed tablet.

Therefore the present invention relates to the use of at least one solid particle (SP), (SP'), (SP1), (SP2), (SP3), (SP4), (SP5), (SP6), (SP7), (SP7'), (SP7"), (SP8), (SP9), (SP10) and/or (SP11) in the production of compressed tablets.

The pressure, which is used to producing tablets, is at least 5 kN

The pressure, which is used to producing tablets, is usually between 5 and 40 kN, preferably between 10-40 kN, more preferably between 5-40 kN.

Therefore the present invention relates to the process (P) of producing compressed tables wherein at least one solid particle (SP), (SP'), (SP1), (SP2), (SP3), (SP4), (SP5), (SP6), (SP7), (SP7'), (SP7"), (SP8), (SP9), (SP10) and/or (SP11) are compressed with at pressure of at least 5 kN.

Therefore the present invention relates to the process (P') of producing compressed tables wherein at least one solid particle (SP), (SP'), (SP1), (SP2), (SP3), (SP4), (SP5), (SP6), (SP7), (SP7'), (SP7"), (SP8), (SP9), (SP10) and/or (SP11) are compressed with at pressure of between 5 and 40 kN.

Therefore the present invention relates to the process (P") of producing compressed tables wherein at least one solid particle (SP), (SP'), (SP1), (SP2), (SP3), (SP4), (SP5), (SP6), (SP7), (SP7'), (SP7"), (SP8), (SP9), (SP10) and/or (SP11) are compressed with at pressure of between 10-40 kN.

Therefore the present invention relates to the process (P''') of producing compressed tables wherein at least one solid particle (SP), (SP'), (SP1), (SP2), (SP3), (SP4), (SP5), (SP6), (SP7), (SP7'), (SP7"), (SP8), (SP9), (SP10) and/or (SP11) are compressed with at pressure of between 15-40 kN.

It is also possible to add any further ingredients (such as fillers, dyestuffs, antioxidants, flavours, etc.) to the solid particles according to the present invention before compressing the particles into the tablet.

Therefore the present invention relates to the process (P1), which is process (P), (P'), (P") or (P'''), wherein at least one further ingredient is added.

The tablet can be a dietary supplement or a pharmaceutical product. This depends what is added to the compressed tablets additionally.

Furthermore the present invention also relates to compressed tablets comprising at least one solid particle (SP), (SP'), (SP1), (SP2), (SP3), (SP4), (SP5), (SP6), (SP7), (SP7'), (SP7"), (SP8), (SP9), (SP10) and/or (SP11).

The invention is illustrated by the following Example. All temperatures are given in ° C. and all parts and percentages are related to the weight.

EXAMPLES

Example 1: Food Modified Starch and Trehalose 370.6 g of deionized water were heated up to 60° C.-65° C. in a vessel. 316.75 g of food modified starch and 121.2 g of trehalose were added and the mixture was brought into solution while stirring at 60-65° C. The obtained solution was cooled to 50-55° C. and degassed for 1 hour. Thereupon, 190.82 g of an oil mixture (180.78 g vitamin A acetate, 5.02 g BHT and 5.02 g dl-alpha-tocopherol) were added to the matrix system and emulsified. The temperature of the process was always kept below 65° C. After emulsification the inner phase of the emulsion had an average particle size of about 272 nm (Dv(0.1)=100 nm, Dv(0.5)=272 nm, Dv(0.9)=559 nm), measurement realized by laser diffraction (Malvern 3000). After emulsification the moisture of the emulsion, determined by a halogen moisture analyzer (Mettler Toledo, Type HR73-P), was checked and adapted if necessary. Afterwards 150 g of the emulsion were sprayed into a spray pan containing 1500 g of corn starch using a rotating spray nozzle. The obtained particles were sieved off (150 to 600 μm) from the excess of corn starch and dried at room temperature using a stream off air. The final product particle size after drying was in average 246 μm (Dv(0.1)=198 μm, Dv(0.5)=246 μm, Dv(0.9)=303 μm) measured by laser diffraction (Malvern 3000).

Solid particles with the composition as listed in table 1 have been obtained.

TABLE 1

| Composition | [wt %] |
| --- | --- |
| Vit. A Ac. 2.8 Mio I.U/g | 27.00 |
| dl-alpha-Tocopherol | 0.75 |
| BHT | 0.75 |
| Food modified starch | 47.31 |
| Trehalose | 18.19 |
| Corn Starch | 4.00 |
| Water | 2.00 |
| Total | 100.00 |

Example: 2 Food Modified Starch and Trehalose 381 g of deionized water were heated up to 60° C.-65° C. in a vessel. 316.75 g of food modified starch and 122.2 g of trehalose were added and the mixture was brought into solution while stirring at 60-65° C. The obtained solution was cooled to 50-55° C. and degassed for 1 hour. Thereupon, 190.78 g of vitamin A acetate were added to the matrix system and emulsified. The temperature of the process was always kept below 65° C. After emulsification the inner phase of the emulsion had an average particle size of about 333 nm (Dv(0.1)=175 nm, Dv(0.5)=333 nm, Dv(0.9)=558 nm), measurement realized by laser diffraction (Malvern 3000). After emulsification the moisture of the emulsion, determined by a halogen moisture analyzer (Mettler Toledo, Type HR73-P), was checked and adapted if necessary. Afterwards 150 g of the emulsion were sprayed into a spray pan containing 1500 g of corn starch using a rotating spray nozzle. The obtained particles were sieved off (150 to 600 μm) from the excess of corn starch and dried at room temperature using a stream off air. The final product particle size after drying was in average 180 μm (Dv(0.1)=180 μm, Dv(0.5)=240 μm, Dv(0.9)=321 μm) measured by laser diffraction (Malvern 3000).

Solid particles with the composition as listed in table 21 have been obtained.

TABLE 2

| Composition | [wt %] |
|---|---|
| Vit. A Ac. 2.8 Mio I.U/g | 27.00 |
| Food modified starch | 48.31 |
| Trehalose | 18.19 |
| Corn Starch | 4.00 |
| Water | 2.00 |
| Total | 100.00 |

Example 3: Food Modified Starch and Sucrose 370.6 g of deionized water were heated up to 60° C.-65° C. in a vessel. 317.4 g of food modified starch and 122.1 g of sucrose were added and the mixture was brought into solution while stirring at 60-65° C. The obtained solution was cooled to 50-55° C. and degassed for 1 hour. Thereupon, 197.3 g of an oil mixture (186.9 g vitamin A acetate, 10.4 g BHT) were added to the matrix system and emulsified. The temperature of the process was always kept below 65° C. After emulsification the inner phase of the emulsion had an average particle size of about 276 nm (Dv(0.1)=112 nm, Dv(0.5)=276 nm, Dv(0.9)=516 nm), measurement realized by laser diffraction (Malvern 3000). After emulsification the moisture of the emulsion, determined by a halogen moisture analyzer (Mettler Toledo, Type HR73-P), was checked and adapted if necessary. Afterwards 150 g of the emulsion were sprayed into a spray pan containing 1500 g of corn starch using a rotating spray nozzle. The obtained particles were sieved off (150 to 600 μm) from the excess of corn starch and dried at room temperature using a stream off air. The final product particle size after drying was in average 272 μm (Dv(0.1)=197 μm, Dv(0.5)=272 μm, Dv(0.9)=377 μm) measured by laser diffraction (Malvern 3000).

Solid particles with the composition as listed in Table 3 have been obtained

TABLE 3

| Composition | [wt %] |
|---|---|
| Vit. A Ac. 2.8 Mio I.U/g | 27.00 |
| BHT | 1.50 |
| Food modified starch | 45.86 |
| Sucrose | 17.64 |
| Corn Starch | 5.00 |
| Water | 3.00 |
| Total | 100.00 |

Example 4: Gum Acacia and Trehalose 381 g of deionized water were heated up to 60° C.-65° C. in a vessel. 143.78 g of food modified starch and 287.56 g of trehalose were added and the mixture was brought into solution while stirring at 60-65° C. The obtained solution was cooled to 50-55° C. and degassed for 1 hour. Thereupon, 187.68 g of an oil mixture (177.80 g vitamin A acetate, 4.94 g BHT and 4.94 g dl-alpha-tocopherol) were added to the matrix system and emulsified. The temperature of the process was always kept below 65° C. After emulsification the inner phase of the emulsion had an average particle size of about 493 nm (Dv(0.1)=215 nm, Dv(0.5)=493 nm, Dv(0.9)=987 nm), measurement realized by laser diffraction (Malvern 3000). After emulsification the moisture of the emulsion, determined by a halogen moisture analyzer (Mettler Toledo, Type HR73-P), was checked and adapted if necessary. Afterwards 150 g of the emulsion were sprayed into a spray pan containing 1500 g of cornstarch using a rotating spray nozzle. The obtained particles were sieved off (150 to 600 μm) from the excess of corn starch and dried at room temperature using a stream off air. The final product particle size after drying was in average 234 μm (Dv(0.1)= 189 μm, Dv(0.5)=234 μm, Dv(0.9)=293 μm) measured by laser diffraction (Malvern 3000).

Solid particles with the composition as listed in Table 4 have been obtained.

TABLE 4

| Composition | [wt %] |
|---|---|
| Vit. A Ac. 2.8 Mio I.U/g | 27.00 |
| dl-alpha-Tocopherol | 0.75 |
| BHT | 0.75 |
| Gum *acacia* | 21.83 |
| Trehalose | 43.67 |
| Corn Starch | 4.00 |
| Water | 2.00 |
| Total | 100.00 |

Example 5: Stability in Stress Tablets 110.3 g of powder consisting of 27 g of vitamin A acetate particles (as obtained in Example 1), 33.24 g microcrystalline cellulose, 49.86 g calcium phosphate and 0.2 g of magnesium stearate was mixed during 10 min. This end preparation was then compressed with a pressure of 35 KN. The tablets (common disk-shaped; 0.2 g) were stored at room temperature in a closed brown-glass bottle and the vitamin A acetate content determined after 1, 7 and 35 days of storage.

For the purpose to show the superior property of the particles according to the present invention, comparative examples were also carried, wherein instead of trehalose or sucrose other sugars, which are no non-reducing sugars, have been used. These comparative solid particles were prepare as described in Example 1.

The impact of the use of trehalose is far better than other types of plasticizer. This can be seen on the FIGS. 1, 2, and 3. (in tables 5-7, the solid particles are listed. The concentration of the ingredients is the same as in Example 1).

TABLE 5

Compressed tablets as on FIG. 1:

| Graph | Composition of the solid particles | | | |
|---|---|---|---|---|
| 1 | Vitamin A acetate | Food modified starch | Maltodextrin12 | BHT/toco |
| 2 | Vitamin A acetate | Food modified starch | trehalose | BHT/toco |
| 3 | Vitamin A acetate | Food modified starch | sucrose | BHT/toco |

TABLE 6

Figure 2:
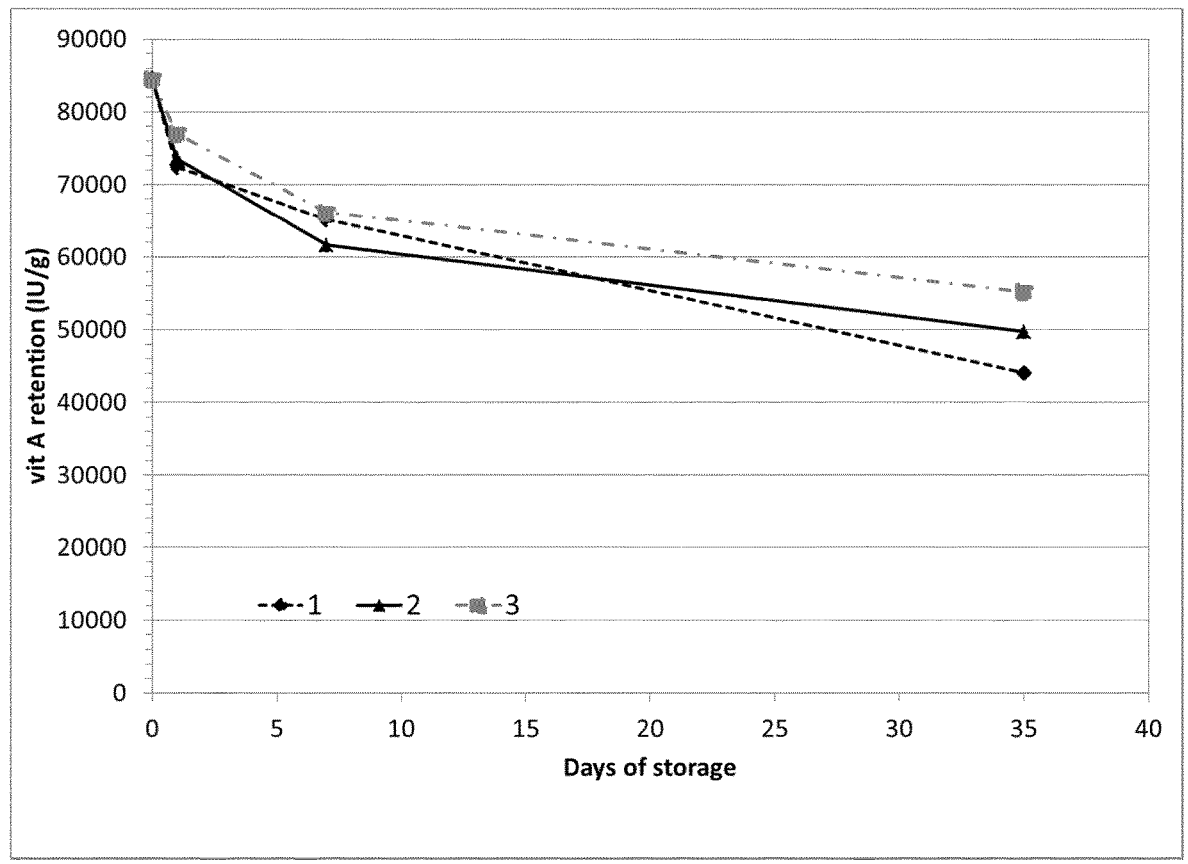

Compressed tablets as on FIG. 2:

| Graph | Composition of the solid particles | | | |
|---|---|---|---|---|
| 1 | Vitamin A acetate | Food modified starches | Maltodextrin 20-23 | BHT/toco |
| 2 | Vitamin A acetate | Food modified starches | Maltodextrin 12 | BHT/toco |
| 3 | Vitamin A acetate | Food modified starch | trehalose | BHT/toco |

TABLE 7

Figure 3:
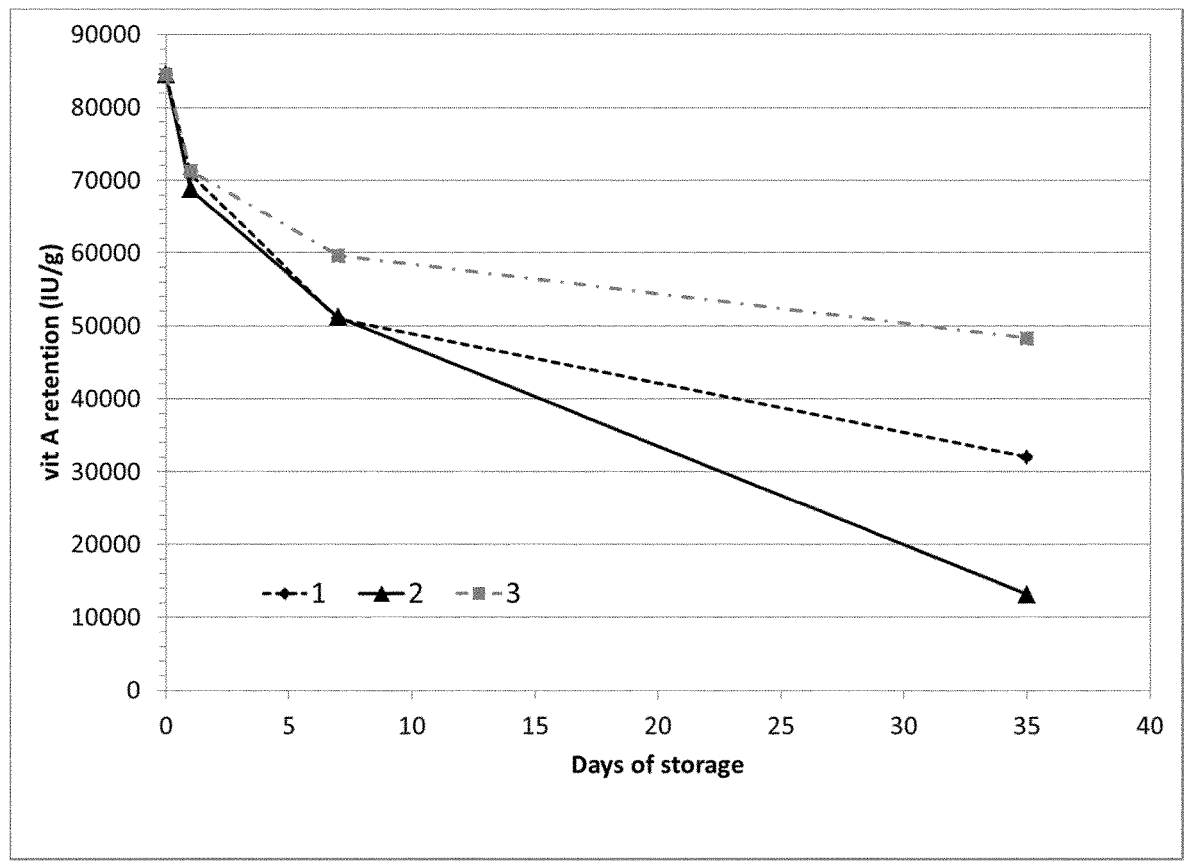

Compressed tablets as on FIG. 3:

| Graph | Composition of the solid particles | | | |
|---|---|---|---|---|
| 1 | Vitamin A acetate | Gum *acacia* | Maltodextrin 20-23 | BHT/toco |
| 2 | Vitamin A acetate | Gum *acacia* | Maltodextrin 12 | BHT/toco |
| 3 | Vitamin A acetate | Gum *acacia* | trehalose | BHT/toco |

The invention claimed is:

1. A compressed tablet consisting of:
   (a) about 24.48 wt. %, based on total weight of the compressed table, of solid particles;
   (b) about 30.14 wt. %, based on total weight of the compressed tablet, of microcrystalline cellulose,
   (c) about 45.20 wt. %, based on total weight of the compressed tablet, of calcium phosphate, and
   (d) about 0.18 wt. %, based on total weight of the compressed tablet, of magnesium stearate, wherein
   the solid particles consist of, based on the total weight of the solid particles, of:
   (i) 27.00 wt. % of vitamin A acetate,
   (ii) 0.75 wt. % of dl-α-tocopherol;
   (iii) 0.75 wt. % of butylated hydroxytoluene (BHT);
   (iii) 47.31 wt. % of food modified starch;
   (iv) 18.19 wt. % of trehalose as a non-reducing sugar;
   (v) 4.00 wt. % of corn starch; and
   (vi) 2.00 wt. % of water, wherein
   the compressed tablet is a compression product of compressing the components (a)-(d) at a pressure between 5-40 kN, and wherein
   the compressed tablet has greater retention of the vitamin A acetate as compared to a similar compressed tablet that does not contain the trehalose after storage in a closed brown-glass bottle at room temperature for 35 days.

2. The compressed tablet according to claim 1, wherein the solid particles have a size Dv90 between 50-1000 μm.

3. The compressed tablet according to claim 2, wherein the solid particles have a size Dv90 between 100-800 μm.

4. The compressed tablet according to claim 1, wherein the tablet is a compression product of compressing the components (a)-(d) at a pressure between 10-40 kN.

* * * * *